United States Patent
McLean et al.

(10) Patent No.: US 12,247,750 B2
(45) Date of Patent: Mar. 11, 2025

(54) WINDOW AIR CONDITIONING AND HEATING UNIT

(71) Applicants: Mark-Anthony McLean, Freeport, NY (US); Audrey Angela McLean, Freeport, NY (US)

(72) Inventors: Mark-Anthony McLean, Freeport, NY (US); Audrey Angela McLean, Freeport, NY (US)

( * ) Notice: Subject to any disclaimer, the term of this patent is extended or adjusted under 35 U.S.C. 154(b) by 971 days.

(21) Appl. No.: 17/196,246

(22) Filed: Mar. 9, 2021

(65) Prior Publication Data
US 2022/0290874 A1    Sep. 15, 2022

(51) Int. Cl.
| | |
|---|---|
| *F02M 25/00* | (2006.01) |
| *A61L 9/00* | (2006.01) |
| *A61L 9/12* | (2006.01) |
| *F24F 1/0284* | (2019.01) |
| *F24F 1/031* | (2019.01) |
| *F24F 1/0328* | (2019.01) |
| *F24F 1/037* | (2019.01) |
| *F24F 11/50* | (2018.01) |
| *F24F 11/58* | (2018.01) |
| *F24F 11/65* | (2018.01) |
| *F24F 6/00* | (2006.01) |

(Continued)

(52) U.S. Cl.
CPC .............. *F24F 1/031* (2019.02); *A61L 9/122* (2013.01); *F24F 1/0284* (2019.02); *F24F 1/0328* (2019.02); *F24F 1/037* (2019.02); *F24F 11/50* (2018.01); *F24F 11/58* (2018.01); *F24F 11/65* (2018.01); *A61L 2209/16* (2013.01); *F24F 2006/008* (2013.01); *F24F 2006/146* (2013.01); *F24F 2110/10* (2018.01); *F24F 2110/20* (2018.01); *H02S 40/38* (2014.12)

(58) Field of Classification Search
CPC .............. F24J 3/085; F24F 6/12; F24F 5/0046
USPC ..................................... 422/5, 306; 261/18.1
See application file for complete search history.

(56) References Cited

U.S. PATENT DOCUMENTS

| | | | |
|---|---|---|---|
| 3,006,613 A | 10/1961 | Coyne | |
| 3,651,864 A * | 3/1972 | Maddox, Jr. ............. | F24F 11/30 165/228 |

(Continued)

FOREIGN PATENT DOCUMENTS

CN            203147924 U  *  8/2013    ................ F24F 1/00

OTHER PUBLICATIONS

Machine English Translation of the Description Section and the Claims Section for CN 203147924 U.*

*Primary Examiner* — Monzer R Chorbaji
(74) *Attorney, Agent, or Firm* — Kyle A. Fletcher, Esq.

(57) ABSTRACT

The window air conditioning and heating unit controls the environmental conditions within a room of a building. The window air conditioning and heating unit mounts in a window of the room. The window air conditioning and heating unit measures and monitors the temperature of and the humidity in the air in the room. The window air conditioning and heating unit comprises an environmental control structure, a control circuit, and a housing. The environmental control structure provides the heat and mass transfer capabilities required to control the temperature and humidity within the room. The control circuit controls and powers the operation of the environmental control structure. The environmental control structure and the control circuit are contained in the housing.

20 Claims, 6 Drawing Sheets

(51) Int. Cl.
*F24F 6/14* (2006.01)
*F24F 110/10* (2018.01)
*F24F 110/20* (2018.01)
*H02S 40/38* (2014.01)

(56) References Cited

U.S. PATENT DOCUMENTS

| | | | |
|---|---|---|---|
| 5,023,020 A * | 6/1991 | Machida | F24F 3/12 |
| | | | 261/DIG. 65 |
| 6,167,714 B1 | 1/2001 | Baffes | |
| 6,466,737 B1 | 10/2002 | Birdsell | |
| 7,639,928 B2 | 12/2009 | Coke | |
| 9,829,896 B1 | 11/2017 | Arend | |
| 10,080,256 B2 | 9/2018 | Kratz | |
| 10,139,119 B2 | 11/2018 | Choi et al. | |
| 10,696,129 B2 | 6/2020 | Sweden | |
| 2011/0262114 A1 | 10/2011 | Montgomery | |
| 2015/0204561 A1 * | 7/2015 | Sadwick | F24F 11/33 |
| | | | 236/1 C |
| 2015/0300696 A1 * | 10/2015 | Gao | F24F 6/043 |
| | | | 62/274 |

* cited by examiner

WINDOW AIR CONDITIONING AND HEATING UNIT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of mechanical engineering including ventilation and heating, more specifically, a self-contained room unit that mounts in a wall opening. (F24F1/027)

SUMMARY OF INVENTION

The window air conditioning and heating unit is an HVAC device. The window air conditioning and heating unit controls the environmental conditions within a room of a building. The window air conditioning and heating unit mounts in a window of the room. By controlling the environmental conditions is meant that the window air conditioning and heating unit will: a) control the temperature within the room; and, b) control the humidity in the room. The window air conditioning and heating unit measures and monitors the temperature of the air in the room. The window air conditioning and heating unit measures and monitors the humidity of the air in the room. The window air conditioning and heating unit maintains the temperature in the room within a first predetermined range. The window air conditioning and heating unit maintains the humidity in the room within a second predetermined range.

The window air conditioning and heating unit comprises an environmental control structure, a control circuit, and a housing. The environmental control structure provides the heat and mass transfer capabilities required to control the temperature and humidity within the room. The control circuit controls and powers the operation of the environmental control structure. The environmental control structure and the control circuit are contained in the housing.

These together with additional objects, features and advantages of the window air conditioning and heating unit will be readily apparent to those of ordinary skill in the art upon reading the following detailed description of the presently preferred, but nonetheless illustrative, embodiments when taken in conjunction with the accompanying drawings.

In this respect, before explaining the current embodiments of the window air conditioning and heating unit in detail, it is to be understood that the window air conditioning and heating unit is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the window air conditioning and heating unit.

It is therefore important that the claims be regarded as including such equivalent construction insofar as they do not depart from the spirit and scope of the window air conditioning and heating unit. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
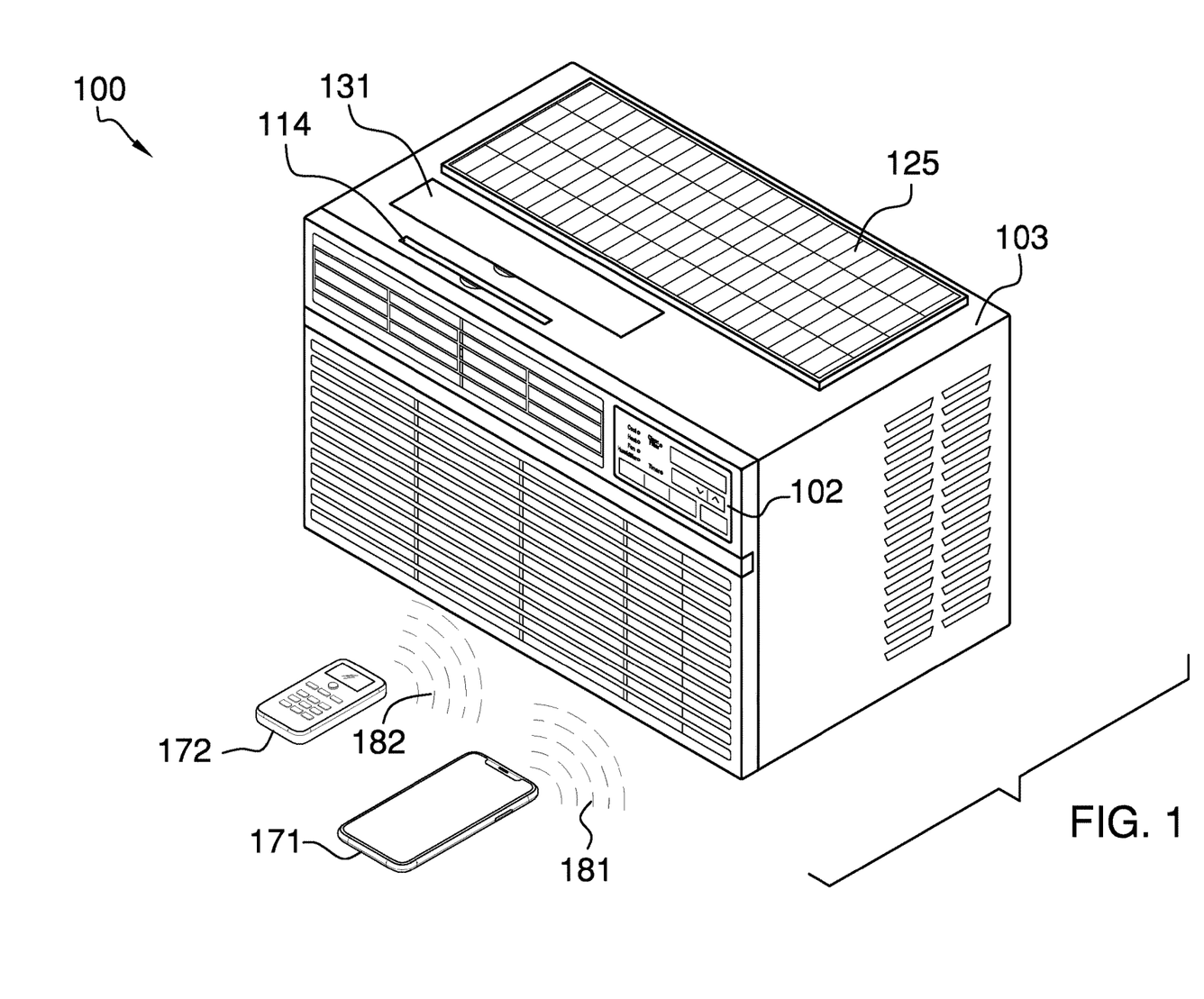
FIG. 1 is a perspective view of an embodiment of the disclosure.
Figure 2:
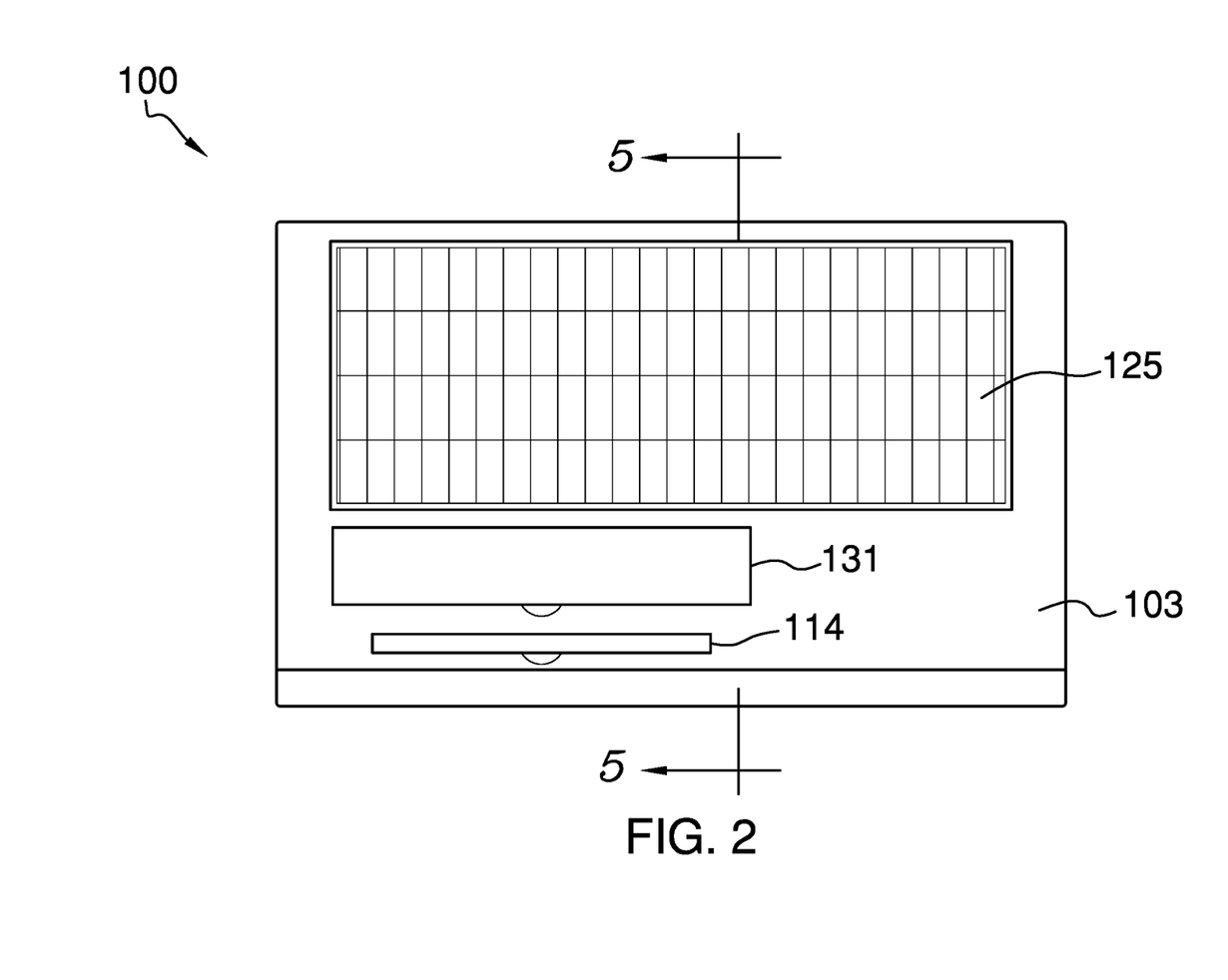
FIG. 2 is a top view of an embodiment of the disclosure.
Figure 3:
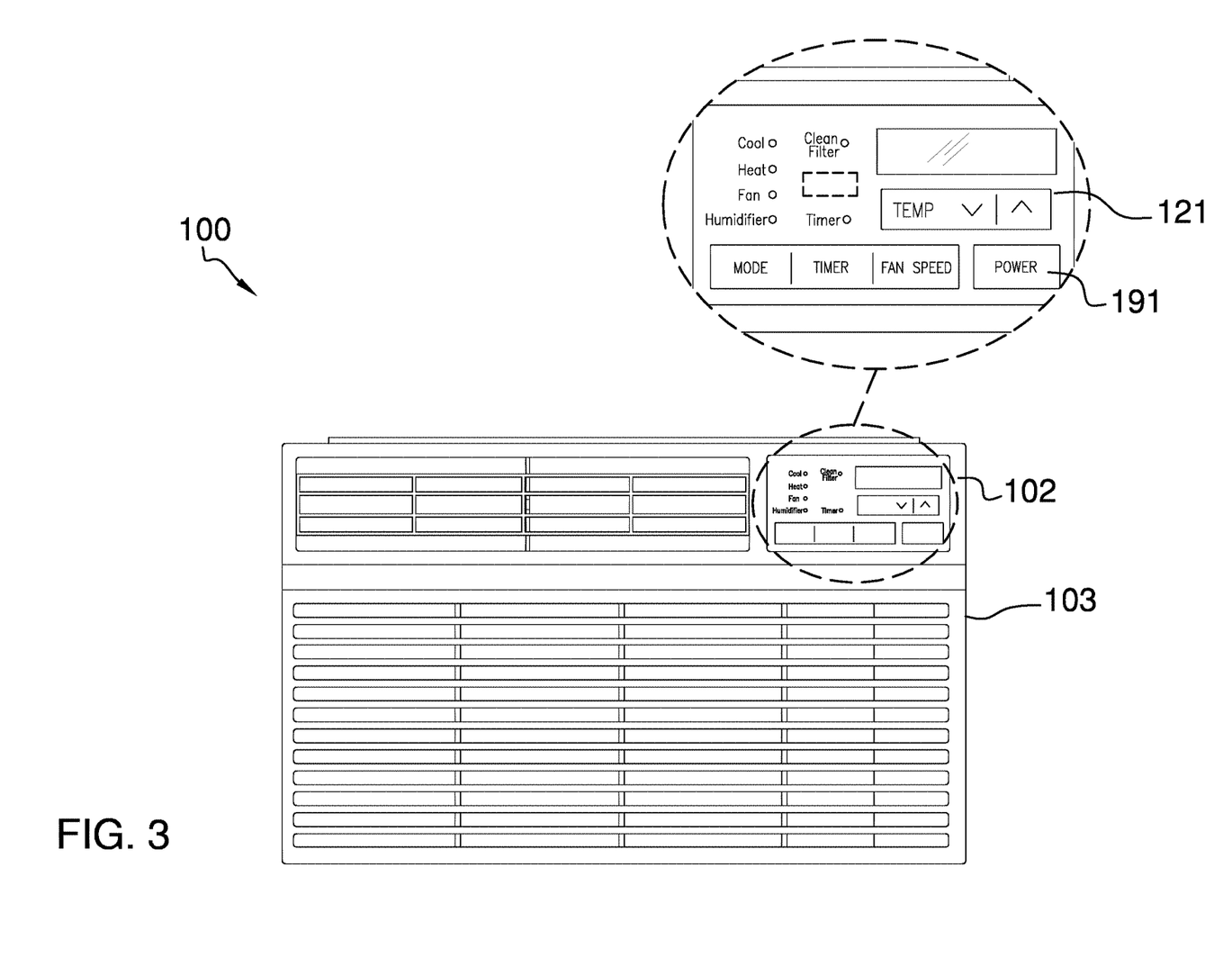
FIG. 3 is a front view of an embodiment of the disclosure.
Figure 4:
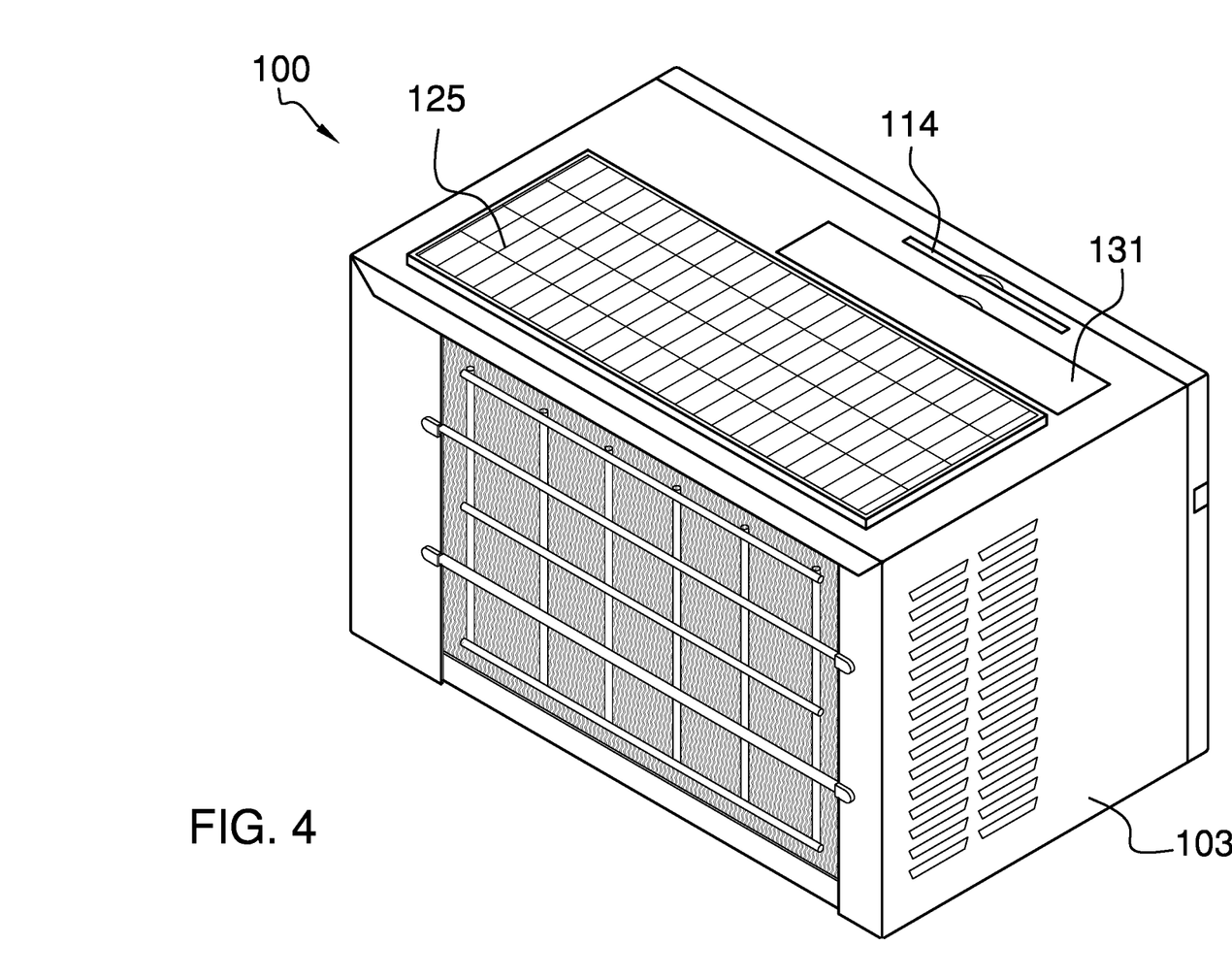
FIG. 4 is a reverse perspective view of an embodiment of the disclosure.
Figure 5:
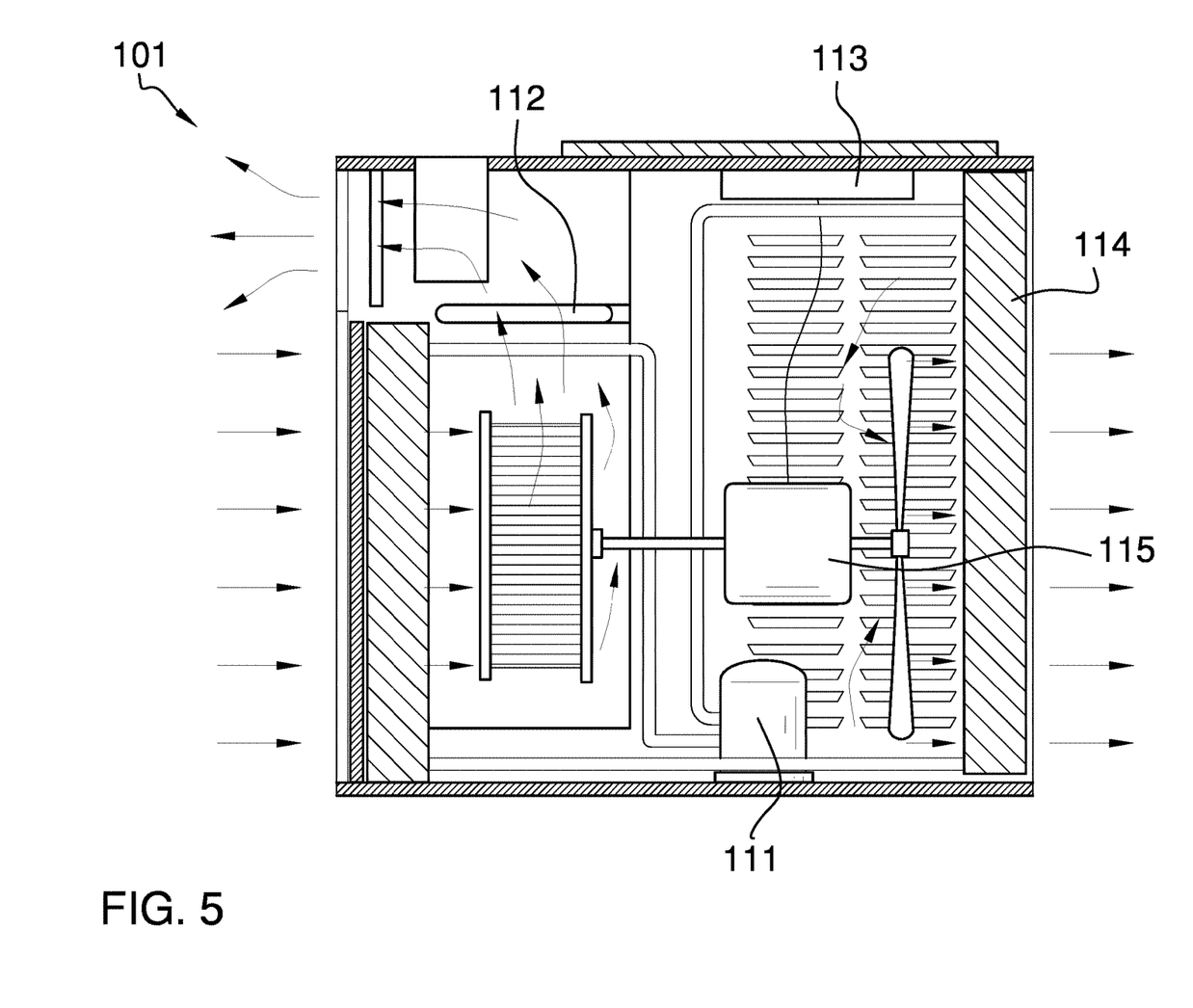
FIG. 5 is a cross-sectional view of an embodiment of the disclosure across 5-5 as shown in FIG. 2.
Figure 6:
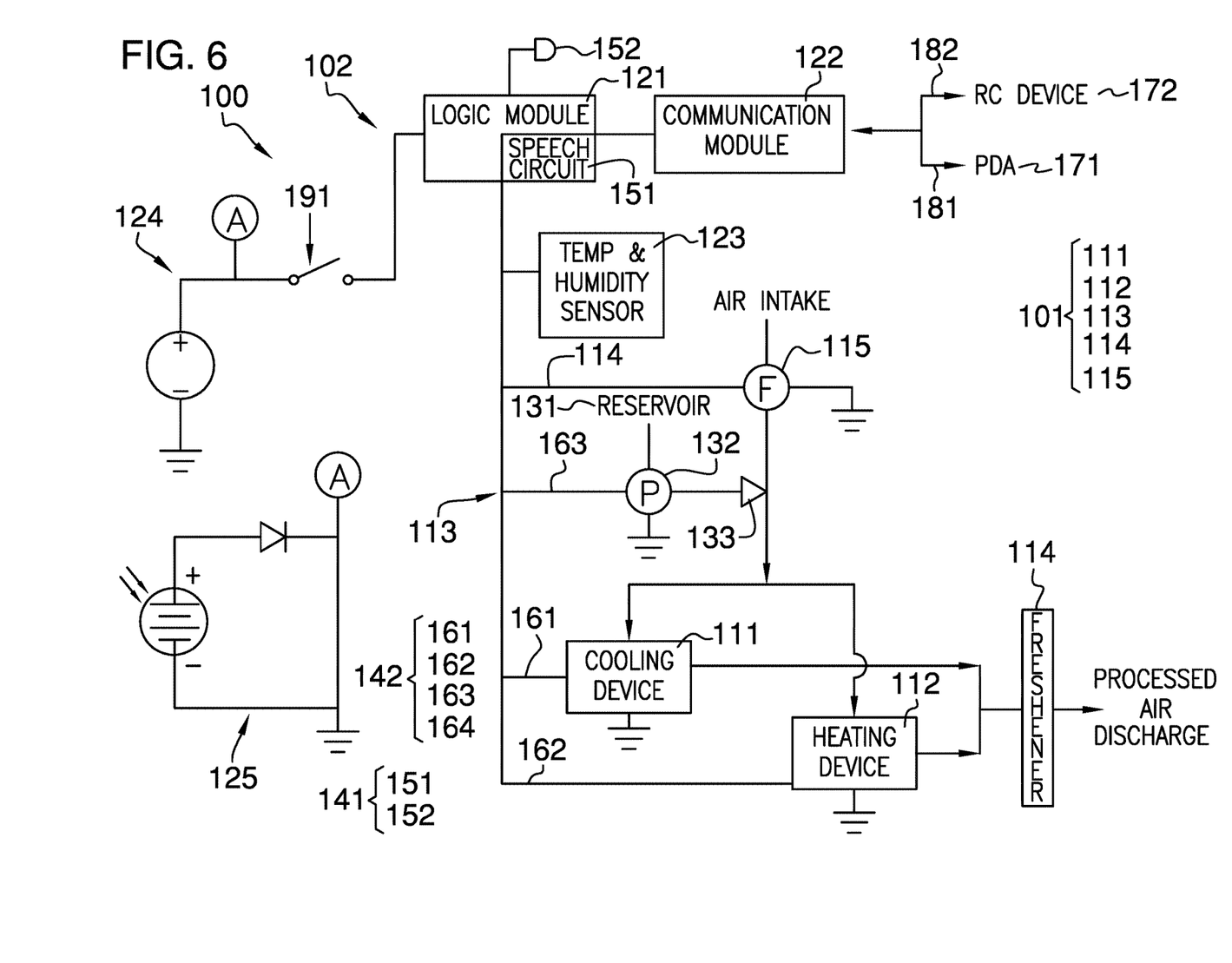
FIG. 6 is a schematic view of an embodiment of the disclosure.

Detailed reference will now be made to one or more potential embodiments of the disclosure, which are illustrated in FIGS. 1 through 6.

The window air conditioning and heating unit 100 (hereinafter invention) is an HVAC device. The invention 100 controls the environmental conditions within a room of a building. The invention 100 mounts in a window of the room. By controlling the environmental conditions is meant that the invention 100 will: a) control the temperature within the room; and, b) control the humidity in the room. The invention 100 measures and monitors the temperature of the air in the room. The invention 100 measures and monitors the humidity of the air in the room. The invention 100 maintains the temperature in the room within a first predetermined range. The invention 100 maintains the humidity in the room within a second predetermined range.

The invention 100 comprises an environmental control structure 101, a control circuit 102, and a housing 103. The environmental control structure 101 provides the heat and mass transfer capabilities required to control the temperature and humidity within the room. The control circuit 102 controls and powers the operation of the environmental control structure 101. The environmental control structure 101 and the control circuit 102 are contained in the housing 103.

The housing 103 is a rigid structure. The housing 103 contains the environmental control structure 101 and the control circuit 102. The housing 103 is formed with all apertures and form factors necessary to allow the housing 103 to accommodate the use and operation of the environmental control structure 101 and the control circuit 102. Methods to form a housing 103 suitable for the purposes described in this disclosure are well-known and documented in the mechanical arts.

The environmental control structure 101 is a mechanical device. The environmental control structure 101 provides the heat and mass transfer mechanisms required to maintain the temperature in the room within a first predetermined range. The environmental control structure 101 provides the heat and mass transfer mechanisms required to maintain the humidity in the room within a second predetermined range. The environmental control structure 101 processes air drawn through an air intake to maintain the temperature and humidity in the room. The environmental control structure 101 discharges the processed air into the room. The environmental control structure 101 further releases an essential oil into the processed air. The environmental control structure 101 comprises a cooling control device 111, a heating control device 112, a humidity control device 113, an air freshening structure 114, and a fan 115.

The cooling control device 111 is a mechanical device. The cooling control device 111 is a device that processes air by cooling the air that passes through the cooling control device 111. The control circuit 102 controls the operation of the cooling control device 111. The control circuit 102 cools the air in the room by cooling the air that flows through the cooling control device 111.

The heating control device 112 is a mechanical device. The heating control device 112 is a device that processes air by heating the air that passes through the heating control device 112. The control circuit 102 controls the operation of the heating control device 112. The control circuit 102 heats the air in the room by heating the air that flows through the heating control device 112.

The humidity control device 113 is a mechanical device. The humidity control device 113 is a device that processes air by adding water vapor into the air that passes through the humidity control device 113. The control circuit 102 controls the operation of the humidity control device 113. The humidity control device 113 comprises a first reservoir 131, a pump 132, and a spray nozzle 133.

The first reservoir 131 is a containment structure. The first reservoir 131 is a fluid impermeable structure. The first reservoir 131 stores water that is introduced into the processed air flow as water vapor by the humidity control device 113. The first reservoir 131 provides the water necessary for the humidity control device 113 to physically maintain the humidity in the room within a second predetermined range. The pump 132 is a mechanical device. The pump 132 generates a pressure differential that transports water from the first reservoir 131 to the spray nozzle 133. The logic module 121 controls the operation of the pump 132. The spray nozzle 133 is a nozzle. The spray nozzle 133 discharges the water received from the pump 132 as a spray directly into the processed air flow. The spray nozzle 133 adds water vapor into the processed air flow to maintain the temperature and humidity in the room.

The air freshening structure 114 is a mechanical structure. The air freshening structure 114 a passive structure that required no electrical energy. The air freshening structure 114 is not controlled by the control circuit 102. The air freshening structure 114 is a second reservoir that contains an essential oil. All the processed air that is discharged by the environmental control structure 101 passes over the reservoir containing the essential oil such that the essential oil evaporates into the flow of the processed air. The essential oil released from the air freshening structure 114 into the processed air flow serves to perfume the air in the room.

The fan 115 is a pump. The fan 115 generates a pressure differential that draws air into the environmental control structure 101 through an air intake. The fan 115 generates the motive forces that pumps the drawn air through the cooling control device 111, the heating control device 112, the humidity control device 113, and the air freshening structure 114 for processing. The fan 115 provides the motive forces that discharge the processed air from the environmental control structure 101.

The control circuit 102 is an electric circuit. The control circuit 102 controls the operation of the environmental control structure 101. The control circuit 102 is a feedback device used to maintain the temperature and humidity in the room. The control circuit 102 measures and monitors the temperature of the air in the room. The control circuit 102 measures and monitors the humidity of the air in the room. The control circuit 102 generates the control signals to the environmental control structure 101 required to maintain the temperature in the room within a first predetermined range. The control circuit 102 generates the control signals to the environmental control structure 101 required to maintain the humidity in the room within a second predetermined range. The control circuit 102 provides the electricity required to power the heat and mass transfer operations of the environmental control structure 101.

The control circuit 102 comprises a logic module 121, a communication module 122, a temperature and humidity sensor 123, and an external power source 124. The logic module 121, the communication module 122, the temperature and humidity sensor 123, and the external power source 124 are electrically interconnected.

The logic module 121 is a readily and commercially available programmable electronic device that is used to manage, regulate, and operate the control circuit 102. Depending on the specific design and the selected components, the logic module 121 can be a separate component within the control circuit 102 or the functions of the logic module 121 can be incorporated into another component within the control circuit 102.

The communication module 122 exchanges operating information and instruction with both a personal data device 171 and a remote control device 172. The communication module 122 creates a first wireless communication link 181 with the personal data device 171. The communication module 122 creates a second wireless communication link 182 with the remote control device 172.

The communication module 122 is a wireless electronic communication device that allows the logic module 121 to wirelessly communicate with a personal data device 171. Specifically, the communication module 122 establishes the first wireless communication link 181 between the control circuit 102 and the personal data device 171. The personal data device 171 transmits operating instructions to the logic module 121 over the first wireless communication link 181.

The communication module 122 allows the logic module 121 to wirelessly communicate with a remote control device 172. The communication module 122 establishes the second wireless communication link 182 between the control circuit 102 and the remote control device 172. The remote control device 172 transmits operating instructions to the logic module 121 over the second wireless communication link 182.

The personal data device 171 is a programmable electrical device that provides data management and communication services through one or more functions referred to as an application. The application is a set of logical operating instructions that are performed by the personal data device 171. The addition of an application will provide increased functionality for the personal data device 171. This disclosure assumes that an application exists for the purpose of interacting with the invention 100. Methods to design and implement an application on a personal data device 171 are well known and documented in the electrical arts.

The logic module 121 is an electric circuit. The logic module 121 controls the operation of the environmental control structure 101. The logic module 121 is a feedback device used to maintain the temperature and humidity in the room. The logic module 121 measures and monitors the temperature of the air in the room.

The logic module 121 measures and monitors the humidity of the air in the room. The logic module 121 transmits the energy and the control signals to the cooling control device 111 and the heating control device 112 required to maintain the temperature in the room within a first predetermined range. The logic module 121 transmits the energy and the control signals to the humidity control device 113 required to maintain the humidity in the room within a second predetermined range. The logic module 121 monitors and controls the operation of the communication module 122. The logic module 121 receives operating instructions from the personal data device 171 and the remote control device 172 through the communication module 122. The logic module 121 receives operating data to the personal data device 171 through the communication module 122.

The logic module 121 further comprises a speech recognition device 141 and a plurality of control signals 142. The speech recognition device 141 is a programmable electric circuit that is operated within the logic module 121. Each of the plurality of control signals 142 is an electric control signal generated by the logic module 121.

The speech recognition device 141 is an electric circuit. The speech recognition device 141 is maintained in the logic module 121. The speech recognition device 141 monitors the sounds in the vicinity of the invention 100. The speech recognition device 141 analyzes the sounds in the vicinity of the invention 100 to determine if a voice command has been issued. If the speech recognition device 141 determines that a voice command has been issued, the speech recognition device 141 instructs the logic module 121 to initiate the processes necessary to perform the spoken instruction. The speech recognition device 141 further comprises a microphone 151 and a speech recognition circuit 152. The microphone 151 and the speech recognition circuit 152 are electrically connected.

The microphone 151 is a transducer. The microphone 151 detects acoustic energy in the vicinity of the invention 100 and converts the detected acoustic energy into an electric signal that is transmitted to the speech recognition circuit 152. The speech recognition circuit 152 is an electric circuit. The speech recognition circuit 152 receives the electric signal from the microphone 151. The speech recognition circuit 152 processes the received electric signal through a speech recognition procedure to determine if a voice command has been given. The speech recognition circuit 152 initiates the operation of the appropriate processes by the logic module 121 when the speech recognition circuit 152 detects the receipt of a voice command.

Each of the plurality of control signals 142 is an electric signal that is generated by the logic module 121. Each of the plurality of control signals 142 initiates the operation of an element of the environmental control structure 101. The plurality of control signals 142 discontinues the operation of the associated element of the environmental control structure 101. The plurality of control signals 142 comprises a cooling control signal 161, a heating control signal 162, a pump 132 control signal 163, and a fan 115 control signal 164. The cooling control signal 161 controls the operation of the cooling control device 111. The heating control signal 162 controls the operation of the heating control device 112. The pump 132 control signal 163 controls the operation of the humidity control device 113. The fan 115 control signal 164 controls the operation of the fan 115.

The cooling control signal 161 is an electric signal generated by the logic module 121. The logic module 121 uses the cooling control signal 161 to initiate the operation of the cooling control device 111. The logic module 121 uses the cooling control signal 161 to discontinue the operation of the cooling control device 111.

The heating control signal 162 is an electric signal generated by the logic module 121. The logic module 121 uses the heating control signal 162 to initiate the operation of the heating control device 112. The logic module 121 uses the heating control signal 162 to discontinue the operation of the heating control device 112.

The pump 132 control signal 163 is an electric signal generated by the logic module 121. The logic module 121 uses the pump 132 control signal 163 to initiate the operation of the pump 132 of the humidity control device 113. The logic module 121 uses the pump 132 control signal 163 to discontinue the operation of the pump 132 of the humidity control device 113.

The fan 115 control signal 164 is an electric signal generated by the logic module 121. The logic module 121 uses the fan 115 control signal 164 to initiate the operation of the fan 115. The logic module 121 uses the fan 115 control signal 164 to discontinue the operation of the fan 115.

The temperature and humidity sensor 123 is an electric device. The temperature and humidity sensor 123 is a sensor. The temperature and humidity sensor 123 electrically connects to the logic module 121. The temperature and humidity sensor 123 measures the temperature and humidity of the room. The temperature and humidity sensor 123 transmits the measured temperature and humidity to the logic module 121. In the first potential embodiment of the disclosure, the temperature and humidity sensor 123 is a single commercially available electric circuit such as the RHT03 sensor available from MaxDetect Technologies Ltd.

The external power source 124 forms the source of electrical energy that powers the operation of the invention 100. The flow of electric energy from the external power source 124 into the invention 100 is controlled by a master switch 191. The master switch 191 is a maintained switch that function as the power switch for the invention 100.

In a second potential embodiment of the disclosure, the external power source 124 is a photovoltaic power source 125. The photovoltaic power source 125 is an electric circuit. The photovoltaic power source 125 uses a photovoltaic cell to convert electromagnetic radiation in the form of light into electric energy. The photovoltaic power source 125 stores the converted electric energy into chemical potential energy that is stored in a battery. The photovoltaic power source 125 further comprises a diode that prevents the flow of electricity from the battery into the photovoltaic cell. The photovoltaic power source 125 is suitable for use as the external power source 124.

The following definitions were used in this disclosure:

Atmosphere: As used in this disclosure, the atmosphere refers to a blanket of gases (primarily nitrogen and oxygen) that surround the earth. Typical atmospheric conditions are approximated and characterized as the normal temperature and pressure. Atmospheric gases are commonly called air.

Battery: As used in this disclosure, a battery is a chemical device consisting of one or more cells, in which chemical energy is converted into electricity and used as a source of power. Batteries are commonly defined with a positive terminal and a negative terminal.

Bluetooth™: As used in this disclosure, Bluetooth™ is a standardized communication protocol that is used to wirelessly interconnect electronic devices.

Communication Link: As used in this disclosure, a communication link refers to the structured exchange of data between two objects.

Control Circuit: As used in this disclosure, a control circuit is an electrical circuit that manages and regulates the behavior or operation of a device.

Diode: As used in this disclosure, a diode is a two terminal semiconductor device that allows current flow in only one direction. The two terminals are called the anode and the cathode. Electric current is allowed to pass from the anode to the cathode.

Essential Oil: As used in this disclosure, an essential oil is a lipid based solution that contains one or more volatile aroma compounds dissolved in a non-polar solvent. Examples of naturally occurring essential oils include, but are not limited to, basil oil, black pepper oil, caraway oil, cannabis flower oil, cedar wood oil, cinnamon oil, citronella oil, chamomile oil, clove oil, davana oil, eucalyptus oil, frankincense oil, horseradish oil, jasmine oil, lavender oil, lemon oil, lemongrass oil, mandarin oil, nutmeg oil, orange oil, oregano oil, peppermint oil, pine oil, sage oil, sandalwood oil, star anise oil, and thyme oil. Basil oil, cedar wood oil, citronella oil, chamomile oil, clove oil, lavender oil, lemongrass oil, and peppermint oil are traditionally considered to have insect repellent and insecticide properties.

External Power Source: As used in this disclosure, an external power source is a source of the energy that is externally provided to enable the operation of the present disclosure. Examples of external power sources include, but are not limited to, electrical power sources and compressed air sources.

Fan: As used in this disclosure, a fan is a pump that moves a gas. The first potential embodiment of this disclosure assumes that the fan is a mechanical device with rotating blades that is used to create a flow or current of a gas.

Feedback: As used in this disclosure, feedback refers to a system, including engineered systems, or a subsystem further comprising an "input" and an "output" wherein the difference between the output of the engineered system or subsystem and a reference is used as, or fed back into, a portion of the input of the system or subsystem. Examples of feedback in engineered systems include, but are not limited to, a fluid level control device such as those typically used in a toilet tank, a cruise control in an automobile, a fly ball governor, a thermostat, and almost any electronic device that comprises an amplifier. Feedback systems in nature include, but are not limited to, thermal regulation in animals and blood clotting in animals (wherein the platelets involved in blood clotting release chemical to attract other platelets).

Form Factor: As used in this disclosure, the term form factor refers to the size and shape of an object.

Housing: As used in this disclosure, a housing is a rigid structure that encloses and protects one or more devices.

Humidity: As used in this disclosure, humidity refers to water vapor that is dissolved in the atmosphere. The mass of water dissolved into the atmosphere is limited by the temperature of the atmosphere.

HVAC: As used in this disclosure, HVAC is an acronym for Heating Ventilation and Air Conditioning and is a general term that refers to the air handling technology used within buildings.

Logic Module: As used in this disclosure, a logic module is a readily and commercially available electrical device that accepts digital and analog inputs, processes the digital and analog inputs according to previously specified logical processes and provides the results of these previously specified logical processes as digital or analog outputs. The disclosure allows, but does not assume, that the logic module is programmable.

Maintained Switch: A used in this disclosure, a maintained switch is a switch that maintains the position that was set in the most recent switch actuation. A maintained switch works in an opposite manner to a momentary switch.

Microphone: As used in this disclosure, a microphone is a transducer that converts the energy from vibration into electrical energy. The sources of vibrations include, but are not limited to, acoustic energy.

Normal Temperature and Pressure: As used in this disclosure, normal temperature and pressure refers to gas storage conditions corresponding to 20 degrees C. at 100 kPa (approx. 1 atmosphere). Normal temperature and pressure is often abbreviated as NTP.

Nozzle: As used in this disclosure, a nozzle is a device that receives fluid under pressure and releases the fluid in a controlled manner into an environment.

Personal Data Device: As used in this disclosure, a personal data device is a handheld logical device that is used for managing personal information and communication. Examples of personal data device include, but are not limited to, cellular phones, tablets, and smartphones. See logical device Photoelectric: As used in this disclosure, photoelectric is an adjective used to describe an electronic component in which the performance of the electronic component is modified by light. Typical photoelectric devices include, but are not limited to, photoelectric transistors, photoelectric diodes, and photoelectric resistors.

Photovoltaic Cell: As used in this disclosure, a photovoltaic cell is a photoelectric device that directly converts light energy into electrical energy.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Remote Control: As used in this disclosure, remote control means the establishment of control of a device from a distance. Remote control is generally accomplished through the use of an electrical device that generates electrically based control signals that are transmitted via radio frequencies or other means to the device.

Reservoir: As used in this disclosure, a reservoir refers to a container or containment system that is configured to store a liquid.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Speech Recognition: As used in this disclosure, an speech recognition refers to a collection of commercially available algorithms that capture process a digital representation of an audible sound in a manner that allows an electronically operated device, such as a computer, to extract data from the digital representation of an audible sound and take a subsequent action based on the data extracted from the audible sound.

Spray: As used in this disclosure, a spray is a plurality of liquid drops dispersed in a gas.

Spray Nozzle: As used in this disclosure, a spray nozzle is a device that receives liquid under pressure and disperses that liquid into the atmosphere as a spray.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Temperature: As used in this disclosure, temperature refers to a relative measure of the kinetic and vibrational energy contained in the atoms and molecules of a first object (or system) relative to the kinetic and vibrational energy contained in the atoms and molecules of a second object (or system). When two objects (or systems) are in thermal equilibrium, the temperature of the two objects (or systems) is the same.

Transducer: As used in this disclosure, a transducer is a device that converts a physical quantity, such as pressure or brightness into an electrical signal or a device that converts an electrical signal into a physical quantity.

Volatile: As used in this disclosure, volatile refers to a substance that will evaporate or sublimate into a gas state at normal temperature and pressure.

WiFi™: As used in this disclosure, WiFi™ refers to the physical implementation of a collection of wireless electronic communication standards commonly referred to as IEEE 802.11x.

Wireless: As used in this disclosure, wireless is an adjective that is used to describe a communication channel between two devices that does not require the use of physical cabling.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A window air conditioning and heating unit comprising an environmental control structure, a control circuit, and a housing;

wherein the environmental control structure and the control circuit are contained in the housing;

wherein the window air conditioning and heating unit controls the environmental conditions within a space;

wherein by controlling the environmental conditions is meant that the window air conditioning and heating unit will: a) control the temperature within the space; and, b) control the humidity in the space;

wherein the environmental control structure comprises a cooling control device, a heating control device, a humidity control device, an air freshening structure, and a fan;

wherein the cooling control device is a device that processes air by cooling the air that passes through the cooling control device;

wherein the heating control device is a device that processes air by heating the air that passes through the heating control device;

wherein the humidity control device is a device that processes air by adding water vapor into the air that passes through the humidity control device;

wherein the fan generates the motive forces that pumps the drawn air through the window air conditioning and heating unit;

wherein the control circuit heats the air in the space by heating the air that flows through the heating control device.

2. The window air conditioning and heating unit according to claim 1 wherein the window air conditioning and heating unit measures and monitors the temperature of the air in the space;

wherein the window air conditioning and heating unit measures and monitors the humidity of the air in the space;

wherein the window air conditioning and heating unit maintains the temperature in the space within a first predetermined range;

wherein the window air conditioning and heating unit maintains the humidity in the space within a second predetermined range;

wherein the environmental control structure provides the heat and mass transfer capabilities required to control the temperature and humidity within the space;

wherein the control circuit controls and powers the operation of the environmental control structure;

wherein the housing is a rigid structure.

3. The window air conditioning and heating unit according to claim 2 wherein the environmental control structure is a mechanical device;

wherein the environmental control structure provides the heat and mass transfer mechanisms required to maintain the temperature in the space within a first predetermined range;

wherein the environmental control structure provides the heat and mass transfer mechanisms required to maintain the humidity in the space within a second predetermined range;

wherein the environmental control structure processes air drawn through an air intake to maintain the temperature and humidity in the space;

wherein the environmental control structure releases an essential oil into the processed air;

wherein the environmental control structure discharges the processed air into the space.

4. The window air conditioning and heating unit according to claim 3 wherein the control circuit is an electric circuit;

wherein the control circuit controls the operation of the environmental control structure;

wherein the control circuit is a feedback device used to maintain the temperature and humidity in the space;

wherein the control circuit measures and monitors the temperature of the air in the space;

wherein the control circuit measures and monitors the humidity of the air in the space;

wherein the control circuit generates the control signals to the environmental control structure required to maintain the temperature in the space within a first predetermined range;

wherein the control circuit generates the control signals to the environmental control structure required to maintain the humidity in the space within a second predetermined range;

wherein the control circuit provides the electricity required to power the heat and mass transfer operations of the environmental control structure.

5. The window air conditioning and heating unit according to claim 4 wherein the air freshening structure contains an essential oil.

6. The window air conditioning and heating unit according to claim 5 wherein the control circuit comprises a logic module, a communication module, a temperature and humidity sensor, and an external power source;

wherein the logic module, the communication module, the temperature and humidity sensor, and the external power source are electrically interconnected.

7. The window air conditioning and heating unit according to claim 6 wherein the cooling control device is a mechanical device;

wherein the control circuit controls the operation of the cooling control device;

wherein the control circuit cools the air in the space by cooling the air that flows through the cooling control device.

8. The window air conditioning and heating unit according to claim 7 wherein the heating control device is a mechanical device;

wherein the control circuit controls the operation of the heating control device.

9. The window air conditioning and heating unit according to claim 8 wherein the humidity control device is a mechanical device;

wherein the control circuit controls the operation of the humidity control device.

10. The window air conditioning and heating unit according to claim 9 wherein the air freshening structure is a mechanical structure;

wherein the air freshening structure a passive structure that required no electrical energy;

wherein the air freshening structure is not controlled by the control circuit;

wherein the air freshening structure is a second reservoir that contains an essential oil;

wherein all the processed air that is discharged by the environmental control structure passes over the reservoir containing the essential oil such that the essential oil evaporates into the flow of the processed air;

wherein the essential oil released from the air freshening structure into the processed air flow serves to perfume the air in the space.

11. The window air conditioning and heating unit according to claim 10 wherein the humidity control device comprises a first reservoir, a pump, and a spray nozzle;

wherein the first reservoir is a containment structure;

wherein the first reservoir is a fluid impermeable structure;

wherein the first reservoir stores water that is introduced into the processed air flow as water vapor by the humidity control device;

wherein the first reservoir provides the water necessary for the humidity control device to physically maintain the humidity in the space within a second predetermined range;

wherein the pump is a mechanical device;

wherein the pump generates a pressure differential that transports water from the first reservoir to the spray nozzle;

wherein the logic module controls the operation of the pump;

wherein the spray nozzle is a nozzle;

wherein the spray nozzle discharges the water received from the pump as a spray directly into the processed air flow;

wherein the spray nozzle adds water vapor into the processed air flow to maintain the temperature and humidity in the space.

12. The window air conditioning and heating unit according to claim 11 wherein the fan is a pump;

wherein the fan generates a pressure differential that draws air into the environmental control structure through an air intake;

wherein the fan generates the motive forces that pumps the drawn air through the cooling control device, the heating control device, the humidity control device, and the air freshening structure for processing;

wherein the fan provides the motive forces that discharge the processed air from the environmental control structure.

13. The window air conditioning and heating unit according to claim 12 wherein the logic module is a programmable electronic device;

wherein the communication module exchanges operating information and instruction with both a personal data device and a remote control device;

wherein the communication module creates a first wireless communication link with the personal data device;

wherein the communication module creates a second wireless communication link with the remote control device;

wherein the communication module is a wireless electronic communication device that allows the logic module to wirelessly communicate with a personal data device;
wherein specifically, the communication module establishes the first wireless communication link between the control circuit and the personal data device;
wherein the personal data device transmits operating instructions to the logic module over the first wireless communication link;
wherein the communication module allows the logic module to wirelessly communicate with a remote control device;
wherein the communication module establishes the second wireless communication link between the control circuit and the remote control device;
wherein the remote control device transmits operating instructions to the logic module over the second wireless communication link.

14. The window air conditioning and heating unit according to claim 13
wherein the logic module is an electric circuit;
wherein the logic module controls the operation of the environmental control structure;
wherein the logic module is a feedback device used to maintain the temperature and humidity in the space;
wherein the logic module measures and monitors the temperature of the air in the space;
wherein the logic module measures and monitors the humidity of the air in the space;
wherein the logic module transmits the energy and the control signals to the cooling control device and the heating control device required to maintain the temperature in the space within a first predetermined range;
wherein the logic module transmits the energy and the control signals to the humidity control device required to maintain the humidity in the space within a second predetermined range;
wherein the logic module monitors and controls the operation of the communication module;
wherein the logic module receives operating instructions from the personal data device and the remote control device through the communication module.

15. The window air conditioning and heating unit according to claim 14
wherein the temperature and humidity sensor is an electric device;
wherein the temperature and humidity sensor is a sensor;
wherein the temperature and humidity sensor electrically connects to the logic module;
wherein the temperature and humidity sensor measures the temperature and humidity of the space;
wherein the temperature and humidity sensor transmits the measured temperature and humidity to the logic module.

16. The window air conditioning and heating unit according to claim 15
wherein the logic module further comprises a speech recognition device and a plurality of control signals;
wherein the speech recognition device is a programmable electric circuit that is operated within the logic module;
wherein each of the plurality of control signals is an electric control signal generated by the logic module;
wherein the speech recognition device is an electric circuit;
wherein the speech recognition device is maintained in the logic module;
wherein the speech recognition device monitors the sounds in the vicinity of the window air conditioning and heating unit;
wherein the speech recognition device analyzes the sounds in the vicinity of the window air conditioning and heating unit to determine if a voice command has been issued;
wherein if the speech recognition device determines that a voice command has been issued, the speech recognition device instructs the logic module to initiate the processes necessary to perform the spoken instruction;
wherein each of the plurality of control signals is an electric signal that is generated by the logic module;
wherein each of the plurality of control signals initiates the operation of an element of the environmental control structure;
wherein the plurality of control signals discontinues the operation of the associated element of the environmental control structure.

17. The window air conditioning and heating unit according to claim 16
wherein the speech recognition device further comprises a microphone and a speech recognition circuit;
wherein the microphone and the speech recognition circuit are electrically connected;
wherein the microphone is a transducer;
wherein the microphone detects acoustic energy in the vicinity of the window air conditioning and heating unit and converts the detected acoustic energy into an electric signal that is transmitted to the speech recognition circuit;
wherein the speech recognition circuit is an electric circuit;
wherein the speech recognition circuit receives the electric signal from the microphone;
wherein the speech recognition circuit processes the received electric signal through a speech recognition procedure to determine if a voice command has been given;
wherein the speech recognition circuit initiates the operation of the appropriate processes by the logic module when the speech recognition circuit detects the receipt of a voice command.

18. The window air conditioning and heating unit according to claim 17
wherein the plurality of control signals comprises a cooling control signal, a heating control signal, a pump control signal, and a fan control signal;
wherein the cooling control signal controls the operation of the cooling control device;
wherein the heating control signal controls the operation of the heating control device;
wherein the pump control signal controls the operation of the humidity control device;
wherein the fan control signal controls the operation of the fan;
wherein the cooling control signal is an electric signal generated by the logic module;
wherein the logic module uses the cooling control signal to initiate the operation of the cooling control device;
wherein the logic module uses the cooling control signal to discontinue the operation of the cooling control device;
wherein the heating control signal is an electric signal generated by the logic module;
wherein the logic module uses the heating control signal to initiate the operation of the heating control device;

wherein the logic module uses the heating control signal to discontinue the operation of the heating control device;

wherein the pump control signal is an electric signal generated by the logic module;

wherein the logic module uses the pump control signal to initiate the operation of the pump of the humidity control device;

wherein the logic module uses the pump control signal to discontinue the operation of the pump of the humidity control device;

wherein the fan control signal is an electric signal generated by the logic module;

wherein the logic module uses the fan control signal to initiate the operation of the fan;

wherein the logic module uses the fan control signal to discontinue the operation of the fan.

19. The window air conditioning and heating unit according to claim 18 wherein the external power source forms the source of electrical energy that powers the operation of the window air conditioning and heating unit;

wherein the flow of electric energy from the external power source into the window air conditioning and heating unit is controlled by a master switch;

wherein the master switch is a maintained switch that function as the power switch for the window air conditioning and heating unit.

20. The window air conditioning and heating unit according to claim 19 wherein the external power source is a photovoltaic power source;

wherein the photovoltaic power source is an electric circuit;

wherein the photovoltaic power source uses a photovoltaic cell to convert electromagnetic radiation in the form of light into electric energy;

wherein the photovoltaic power source stores the converted electric energy into chemical potential energy that is stored in a battery;

wherein the photovoltaic power source further comprises a diode that prevents the flow of electricity from the battery into the photovoltaic cell.

\* \* \* \* \*